(12) United States Patent
Jenkins et al.

(10) Patent No.: US 8,900,230 B2
(45) Date of Patent: Dec. 2, 2014

(54) BIPOLAR SURGICAL MORCELLATOR

(75) Inventors: Andrew E. Jenkins, Mid Glamorgan (GB); Hollie E. Johnston, Wiltshire (GB); Alistair I. Fleming, Cambridgeshire (GB)

(73) Assignee: Gyrus Medical Limited, Cardiff (GB)

( * ) Notice: Subject to any disclaimer, the term of this patent is extended or adjusted under 35 U.S.C. 154(b) by 1102 days.

(21) Appl. No.: 12/761,211

(22) Filed: Apr. 15, 2010

(65) Prior Publication Data

US 2011/0184409 A1    Jul. 28, 2011

(30) Foreign Application Priority Data

Apr. 16, 2009 (GB) .................................. 0906572.3

(51) Int. Cl.
  *A61B 18/14* (2006.01)
  *A61B 18/00* (2006.01)

(52) U.S. Cl.
  CPC ..... *A61B 18/1482* (2013.01); *A61B 2018/1497* (2013.01); *A61B 2018/00083* (2013.01)
  USPC .......................................................... 606/48

(58) Field of Classification Search
  USPC .......................................... 606/27, 34, 41, 48
  See application file for complete search history.

(56) References Cited

U.S. PATENT DOCUMENTS

| | | | | |
|---|---|---|---|---|
| 5,080,660 A | * | 1/1992 | Buelna | 606/45 |
| 5,462,545 A | * | 10/1995 | Wang et al. | 606/41 |
| 5,562,720 A | * | 10/1996 | Stern et al. | 607/98 |
| 5,569,241 A | * | 10/1996 | Edwards | 606/41 |
| 5,599,345 A | * | 2/1997 | Edwards et al. | 606/41 |
| 5,687,723 A | * | 11/1997 | Avitall | 600/374 |
| 5,837,001 A | * | 11/1998 | Mackey | 607/102 |
| 6,007,512 A | | 12/1999 | Hooven | |
| 6,235,023 B1 | * | 5/2001 | Lee et al. | 606/41 |

(Continued)

FOREIGN PATENT DOCUMENTS

| | | |
|---|---|---|
| CN | 120 702 7 | 2/1999 |
| CN | 133 681 2 | 2/2002 |

(Continued)

OTHER PUBLICATIONS

Search Report under Section 17, dated Jul. 23, 2009, Application No. GB0906572.3.
International Search Report for International Application No. PCT/GB2010/000573, Completed Sep. 2, 2010.

(Continued)

*Primary Examiner* — Linda Dvorak
*Assistant Examiner* — Daniel Fowler
(74) *Attorney, Agent, or Firm* — Nixon & Vanderhye P.C.

(57) ABSTRACT

A device for morcellating tissue within a body cavity of a patient comprises a stationary tube (8) having a distal end portion, and a bipolar electrosurgical electrode assembly (13) located at the distal end of the tube. The electrosurgical electrode assembly (13) comprises first and second electrodes (14, 16) separated by an insulation member (15). When an electrosurgical cutting voltage is applied to the electrode assembly (13), and relative movement is initiated between the tube (8) and the tissue, a slug of resected tissue is formed within the tube such that it can be removed from the body cavity of the patient. The bipolar electrosurgical assembly (13) has a first circumferential region (A) and a second circumferential region (B), the first circumferential region (A) being longer than the second circumferential region (B), the bipolar electrosurgical assembly being adapted to cut tissue preferentially in the first circumferential region (A) as compared with the second circumferential region (B).

13 Claims, 5 Drawing Sheets

(56) References Cited

U.S. PATENT DOCUMENTS

| | | | |
|---|---|---|---|
| 6,395,002 | B1 | 5/2002 | Ellman et al. |
| 6,676,659 | B2 * | 1/2004 | Hutchins et al. ................ 606/47 |
| 2002/0049438 | A1 | 4/2002 | Sharkey et al. |
| 2002/0049442 | A1 | 4/2002 | Roberts et al. |
| 2005/0070892 | A1 | 3/2005 | Ciarrocca |
| 2006/0247615 | A1 * | 11/2006 | McCullagh et al. ............ 606/41 |
| 2008/0039883 | A1 | 2/2008 | Nohilly |

FOREIGN PATENT DOCUMENTS

| | | |
|---|---|---|
| CN | 101 277 653 | 10/2008 |
| GB | 2436065 A | 9/2007 |
| WO | 94/00060 A1 | 1/1994 |
| WO | 96/24296 A1 | 8/1996 |
| WO | 01/24720 | 12/2001 |
| WO | 2008/021717 A1 | 2/2008 |

OTHER PUBLICATIONS

Written Opinion of the International Searching Authority for International Application No. PCT/GB2010/000573, Completed Sep. 2, 2010.

Examination Report of Application No. GB1117322.6 dated Mar. 22, 2013.

English Translation of Chinese Search Report dated Jun. 25, 2013 for corresponding Chinese Application No. 201080016894.3.

English Translation of Chinese Office Action issued Jul. 2, 2013 in corresponding Chinese Application No. 201080016894.3.

English Translation of Chinese Notification of Office Action for corresponding First Notification of Office Action; date of issue Jul. 2, 2013.

First Office Action issued Jul. 2, 2013 in Chinese Application No. 201080016894.3.

Search Report dated Jun. 25, 2013 for Chinese Application No. 201080016894.3.

* cited by examiner

BIPOLAR SURGICAL MORCELLATOR

BACKGROUND OF THE INVENTION

This invention relates to a bipolar electrosurgical instrument for use in the bulk removal of tissue, as in a laparoscopic hysterectomy.

In a laparoscopic hysterectomy, the body of the uterus is resected from the stump or fundus, and then removed from the operative site. To enable the uterus to be removed through a limited surgical opening, it is desirable to morcellate it into relatively smaller pieces of tissue, which are easier to remove. Our pending patent application, published as WO05/112806 describes an electrosurgical morcellator for the bulk removal of tissue. The present invention relates to an improvement to this type of instrument.

A known problem with morcellating devices is their tendency to "coring", in which the tip of the morcellator dives into the tissue in a relatively uncontrolled way. A preferred cutting technique is to use the device in a "peeling" action, in which the cutting instrument removes tissue from the outside of an organ, rather like the peeling of an apple or orange. Peeling is preferred to coring for several reasons. A first reason is that the tip of the morcellator is more visible to the surgeon if it is peeling around the outside of the tissue, as opposed to being buried within the tissue as happens when the instrument is producing a core of tissue. Peeling produces a more continuous cut, and also a more continuous mass of uncut tissue. The more continuous cut means that the process can be completed more quickly, with the surgeon having to re-engage the tissue less often. Peeling from the outside of a solid organ or mass of tissue leaves behind a more continuous mass of tissue, and less tissue fragments as compared with coring.

Published US patent application 2008/0039883 describes the problem with coring, and provides a mechanical solution in the form of a protrusion situated at the distal tip of the instrument. The present invention attempts to provide an alternative solution, more suited to use with an electrosurgical morcellator.

SUMMARY OF THE INVENTION

The present invention provides a device for morcellating tissue within a body cavity of a patient, the morcellating device comprising a stationary tube having a distal end portion, the distal end portion including a stationary bipolar electrosurgical electrode assembly including first and second electrodes located at the distal end of the tube and separated one from the other by an insulation member, the arrangement being such that, when an electrosurgical cutting voltage is applied to the electrode assembly, tissue can be pulled against the distal end of the tube to form a slug of resected tissue within the tube, the bipolar electrosurgical assembly having a first circumferential region and a second circumferential region, the first and second electrodes being provided in the first circumferential region, the first circumferential region extending continuously around at least 50% of the tube, and the bipolar electrosurgical assembly being adapted to cut tissue preferentially in the first circumferential region as compared with the second circumferential region.

By providing an electrosurgical cutting assembly in which cutting is performed preferentially in a first circumferential region, and either less effectively or not at all in a second circumferential region, the cutting instrument is unable to cut around the whole of the 360° circumference of the tube. This means that the cutting tip is less likely to be able to remove a core of tissue and become buried within the body of the organ being morcellated. With a section of the tissue being less easily cut, the morcellating instrument removes tissue at the surface of the organ in a more controlled peeling action.

The second circumferential region should not be so great as to substantially affect the cutting capability of the instrument, and so the first circumferential region extends around at least 50% of the circumference of the tube. Other convenient arrangements have the second circumferential region constituting approximately 33%, 20% or even 10% of the circumference of the tube.

A convenient way of ensuring that the second circumferential region cuts less effectively than the first circumferential region is to ensure that the device is such that neither the first electrode nor the second electrode occupies the second circumferential region. In this way, the electrosurgical cutting assembly is unable to perform an effective cut around its entire circumference. Either the first (active) electrode or the second (return) electrode can be provided in this way to disrupt the cutting action.

In one arrangement, an insulator occupies the second circumferential region. Thus, the first (active) electrode or the second (return) electrode extends continuously around the first circumferential region, but is replaced with an insulator in the second circumferential region. The electrosurgical cutting assembly is unable to cut effectively in the region where the first electrode or the second electrode is replaced by an insulator, thereby providing the uncut portion of tissue which is effective in promoting peeling and discouraging coring of tissue.

In an alternative arrangement, the second circumferential region is not merely provided with an insulator instead of the first electrode or the second electrode, but instead comprises a third electrode spaced from both the first and second electrodes by one or more insulating sections. Preferably, the first, second and third electrodes each have separate leads connected thereto, such that the third electrode is capable of being selectively switched in and out of common electrical potential with that of at least one of either the first and second electrodes. In this way, the third electrode can be selectively switched "on" so as to provide a cutting action in collaboration with the first circumferential region, or alternatively switched "off" so as to act as an insulator as previously described. The instrument can, therefore, be controlled by the user, either to peel tissue with the anti-coring system in operation; or, if coring is required for some reason (or if the maximum cutting potential is required for a particularly difficult tissue extraction), the third electrode can be energised to provide cutting around the whole 360° circumference of the tube.

Conceivably, either the first electrode or the second electrode is split into three or more circumferential sections, each separated from adjacent circumferential sections by means of insulators. In this arrangement, the three or more circumferential sections preferably each have separate leads connected thereto, such that each circumferential section is capable of being switched into, and out of, common electrical potential with other circumferential sections. The device preferably carries a switch means capable of changing the circumferential section or sections that are switched out of common electric potential with the other circumferential sections. In this way, any one or more of the three or more circumferential sections can be selectively switched to become insulated from the other sections, and hence become the second circumferential region described heretofore. This arrangement allows the user of the instrument to select which circumferential region of the tube is to become less effective at cutting and hence provide the anti-coring effect. It is, therefore, not necessary for the user to re-orient the tube to accommodate a fixed anti-coring region, and the user is able to change the anti-coring region depending on the orientation of the instrument. It is also possible for the user to increase or decrease the number of sections that are insulated, so as to be able to increase or decrease the anti-coring region as required. Conceivably, the switch means comprises a rotatable collar carried on the device.

Alternatively, there is provided means for determining the orientation of the tube, and for activating the switch means so as to vary the circumferential section or sections that are switched out of common electric potential with the other circumferential sections depending on the orientation of the tube. In this way, the insulated section is maintained in a predetermined orientation, regardless of which way the tube is oriented by the user. For example, it has been found advantageous to maintain the non-cutting section towards the outside of the body of tissue, on the "top" of the device as it is being used. This keeps the morcellator towards the surface of the tissue, and prevents it from becoming buried within the tissue. By automatically orienting the non-cutting section regardless of orientation, the user does not need to make manual adjustments as the device is being used.

In one convenient arrangement, the tube is provided with a marker in alignment with the second circumferential region, to highlight its position to a user of the device. Thus the user always knows which portion of the tube is provided with the anti-coring effect, regardless of whether the circumferential region is fixed or changeable, manually or automatically.

In an alternative arrangement, the second circumferential region is provided by covering the first or second electrode with an electrically-insulating mask. This is in contrast to earlier described arrangements in which the first electrode or the second electrode is interrupted in the second circumferential region, either by an insulating section or by a third electrode. In this alternative arrangement, the first electrode or the second electrode runs continuously around the circumference of the tube, but is masked by the electrically-insulating mask in the second circumferential region. In one arrangement, the mask is selectively detachable from the first electrode or the second electrode. Alternatively, the mask is selectively deployable between a first position in which it obscures the first electrode or the second electrode, and a second position in which it does not obscure the first electrode or the second electrode. Conveniently, the mask is selectively advanced and retracted between the first and second positions. Whichever arrangement is employed, the mask prevents effective cutting of tissue in the second circumferential region and provides the anti-coring effect previously described.

BRIEF DESCRIPTION OF THE DRAWINGS

The invention will now be described in more detail, by way of example, with reference to the drawings, in which.

DESCRIPTION OF PREFERRED EMBODIMENTS

Figure 1:
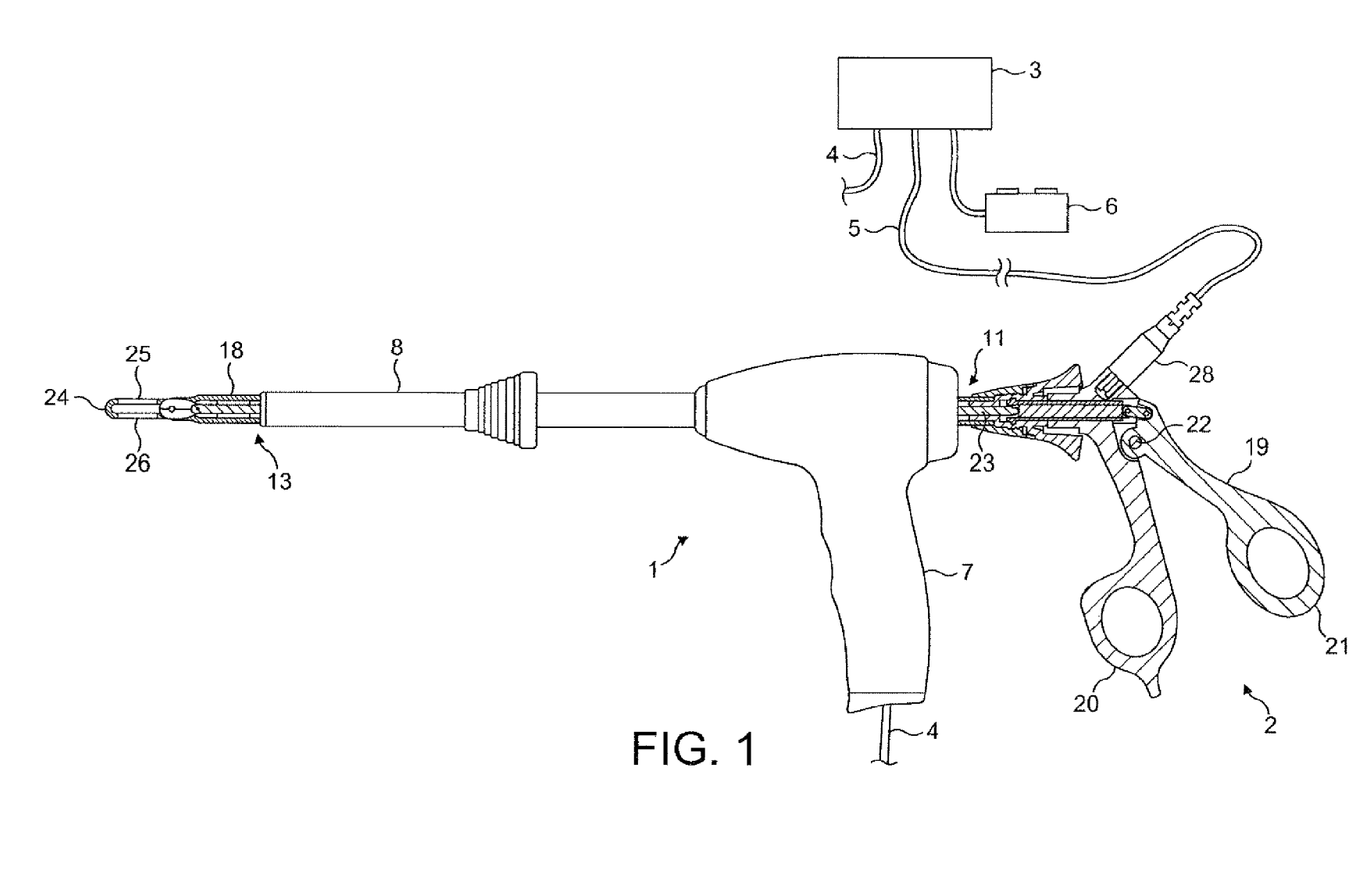
FIG. 1 is a schematic side view, partly in section, of a morcellating device constructed in accordance with the invention.

Referring to FIG. 1, a morcellating system comprises a morcellating device shown generally at 1, a tissue-pulling device shown generally at 2, and an electrosurgical generator 3. The generator 3 is connected to the morcellating device 1 by means of a cable 4, and to the tissue-pulling device 2 by means of a cable 5. The generator 3 is controlled by means of a footswitch 6.

Figure 2:
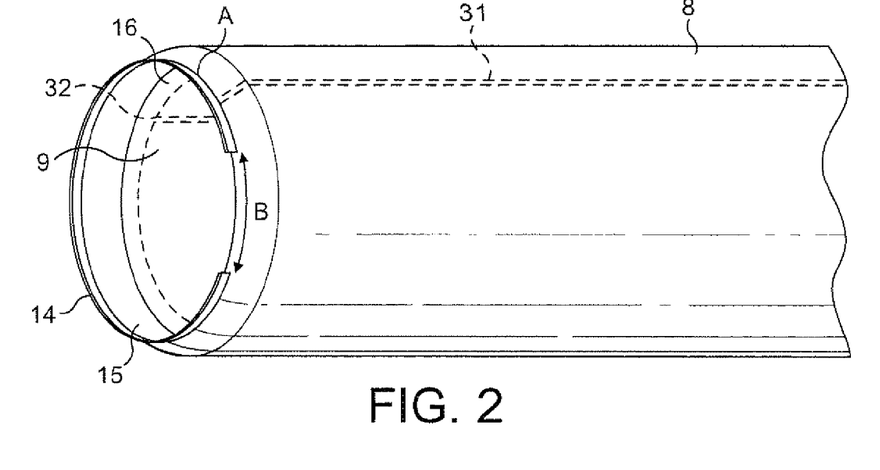
FIG. 2 is an enlarged view of a part of the device shown in FIG. 1.

As shown in FIGS. 1 and 2, the morcellating device 1 comprises a handle 7 and a cylindrical tube 8. The cylindrical tube 8 is hollow, and defines a lumen 9 therein. The proximal end of the tube 8 extends from the handle 7 as shown at 11, and the distal end of the tube is provided with an electrosurgical electrode assembly 13. The electrosurgical electrode assembly 13 comprises an active tissue-cutting electrode 14, and an insulation member 15, both extending around the circumference of the tube 8. The insulation member 15 separates the active electrode 14 from a return electrode 16, also located on the tube 8.

The active electrode 14 extends around the circumference of the tube 8, and is connected to one pole of the generator 3, via the cable 4. The return electrode 16 is connected to the other pole of the generator 3, via the cable 4 and additional wiring (to be described later). In this way, the electrodes 14 and 16 constitute the bipolar electrode assembly 13, which, when energised by the generator 3, is capable of cutting tissue coming into contact with the distal end of the tube 8.

The tissue-pulling device 2 comprises a tubular shaft 18, at the proximal end of which is a scissors-type handle mechanism 19, having a first handle 20 and a second handle 21. The second handle 21 is pivotable with respect to the first handle 20, about a pivot pin 22. Pivoting of the second handle 21 causes longitudinal movement of a push rod 23 extending through the shaft 18 to the distal end thereof.

At the distal end of the shaft 18 is a jaw assembly 24, with a first jaw member 25 and a second jaw member 26 movable between open and closed positions by the movement of the push rod 23. The tissue-pulling device 2 is manually translatable in a longitudinal manner within the lumen 9 of the morcellating device 1. The jaw members 25 and 26 are electrically connected to the shaft 18, and the shaft is optionally electrically connected, via the cable 5 and a connector 28, with the generator 3. The shaft 18 is connected to the same pole of the generator 3 as the return electrode 16.

The operation of the morcellating system is as follows. The tube 8 of the morcellating device 1 is inserted into the body of a patient, typically through a trocar (not shown), or optionally directly into an incision made in the body of the patient. The device 1 is brought into position adjacent to the tissue to be removed, which is typically a resected uterus in the case of a laparoscopic hysterectomy. The tissue-pulling device 2 is then inserted through the lumen 9 of the morcellating device 1. The handle 21 is operated to open the jaw assembly 24, and the tissue-pulling device 2 is maneuvered so that tissue from the uterus is located between the jaw members 25 and 26. The handle 21 is then operated to close the jaw assembly 24, grasping tissue therein.

The surgeon operates the footswitch 6 to operate the generator 3 so that an electrosurgical cutting voltage is supplied between the active electrode 14 and the return electrode 16. As mentioned previously, the push rod 23 and the jaw assembly 24 are also electrically connected to the same pole of the generator 3 as the return electrode 16, and so both the return electrode and the jaw assembly constitute a return. With tissue firmly grasped in the jaw assembly 24, the tissue-pulling device 2 is slowly withdrawn from the tube 8, pulling the tissue against the distal end of the tube and against the active electrode 14. As the tissue contacts the active electrode 14, it is vaporised, allowing the tissue-pulling device 2 to be withdrawn further into the tube 8. In this way, a cylindrical slug of tissue is formed in the tube 8, the tissue being withdrawn though the proximal end 10 of the morcellating device 1 (which remains outside the body of the patient) for disposal.

The tissue-pulling device 2 can then be re-inserted into the tube 8 such that a further slug of tissue can be removed from the body of the patient. By repeating this process, large quantities of tissue can be removed from the patient in a relatively short time, such that the entire uterus can be removed, if necessary, while still employing a laparoscopic approach.

FIG. 2 shows the distal end of the tube 8 according to a first embodiment of the invention, in which the active electrode 14 extends around the circumference of the tube 8 in a first circumferential region A constituting more than 50% of the circumference of the tube, but does not extend into a second circumferential region B constituting less than 50% of the circumference of the tube. In the second circumferential region B there is merely the exposed insulation member 15. The return electrode 16 extends completely around the tube 8 as shown. Leads 31 and 32 respectively connect the electrodes 14 and 16 to the generator 3. When the electrosurgical cutting voltage is supplied between the electrodes 14 and 16, and tissue is pulled against the electrodes by the tissue-pulling device 2, the tissue will be electrosurgically cut in the region A, but remain unsevered in the region B. More and more tissue can be pulled against the tube 8 by the retraction of the tissue-pulling device 2, and the result will be a peeling of tissue with a segment of the tissue remaining connected to the uterus adjacent to the region B. In this way, the tube 8 will remain towards the edge of the uterus, rather than being buried into the tissue to produce a coring action.

Figure 3:
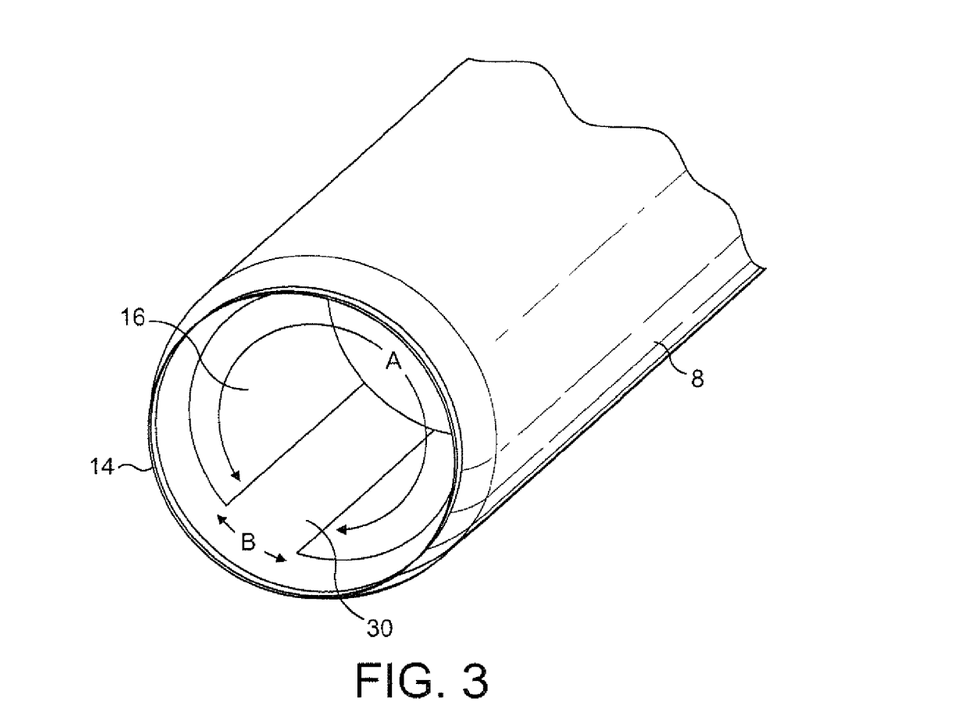
FIG. 3 is an enlarged view of an alternative embodiment of a morcellating device constructed in accordance with the invention.

FIG. 3 shows an alternative distal arrangement in which the active electrode 14 extends continuously around the circumference of the tube 8, but the return electrode 16 extends solely around region A, and is replaced by an insulator 30 in region B. As the electrosurgical cutting action will only be effective where the active and return electrodes 14 and 16 are in close proximity to one another, this arrangement will function in a similar fashion to that of the device of FIG. 2.

Figure 4:
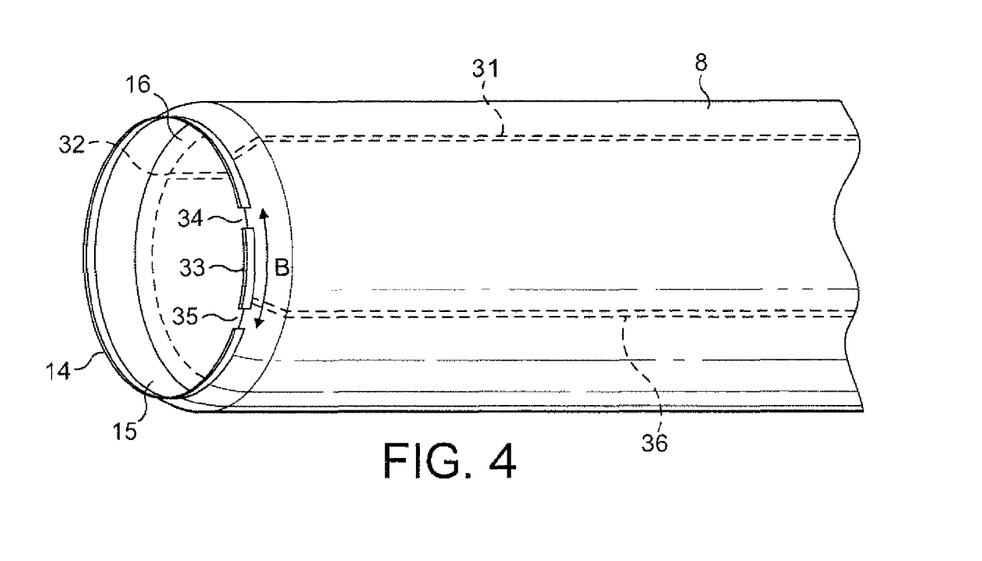
FIG. 4 is an enlarged view of a further embodiment of a morcellating device constructed in accordance with the invention.

FIG. 4 shows a further arrangement, somewhat similar to that of FIG. 3 in that the active electrode 14 extends around the circumference of the tube in a first circumferential region A, but does not extend into a second circumferential region B. However, in the region B there is provided a further active electrode 33 spaced from each circumferential end of the electrode 14 by insulating spacers 34 and 35. The return electrode 16 extends completely around the circumference of the tube 8 as shown. The lead 31 connects the active electrode 14 to the generator 3, the lead 32 connects the return electrode 16 to the generator, and a further lead 36 connects the further electrode 33 to the generator. The further electrode 33 is connected to the generator 3 via a switching device (not shown), the operation of which will now be described.

In a first situation, the switching device is set so that the electrosurgical cutting voltage is supplied solely to the active electrode 14, such that the voltage is supplied between the electrodes 14 and 16 in the region A, with no cutting action being created in the region B. This is the anti-coring cutting action previously described with reference to FIGS. 2 and 3. However, there may be times when the user of the morcellating device 1 needs to provide a cutting action completely around the circumference of the tube 8, either because the user wants to create a coring action, or because the nature of the tissue being treated means that the maximum cutting activity is needed. In this circumstance, the switching device is set so that the electrosurgical cutting voltage is supplied to both active electrodes 14 and 33 such that the voltage is supplied not only between the electrodes 14 and 16 in the region A, but also between the electrodes 33 and 16 in the region B. This means that the cutting action is available around the complete circumference of the tube 8, when desired. In an alternative arrangement, the further active electrode 33 is supplied with a lower voltage than the electrosurgical cutting voltage, such that it is not capable of cutting tissue but perhaps capable of coagulating tissue in combination with the return electrode 16. This will still provide the anti-coring action described previously, and may be useful where the tissue being dissected remains vascular, and where excessive bleeding is to be prevented.

Figure 5A:
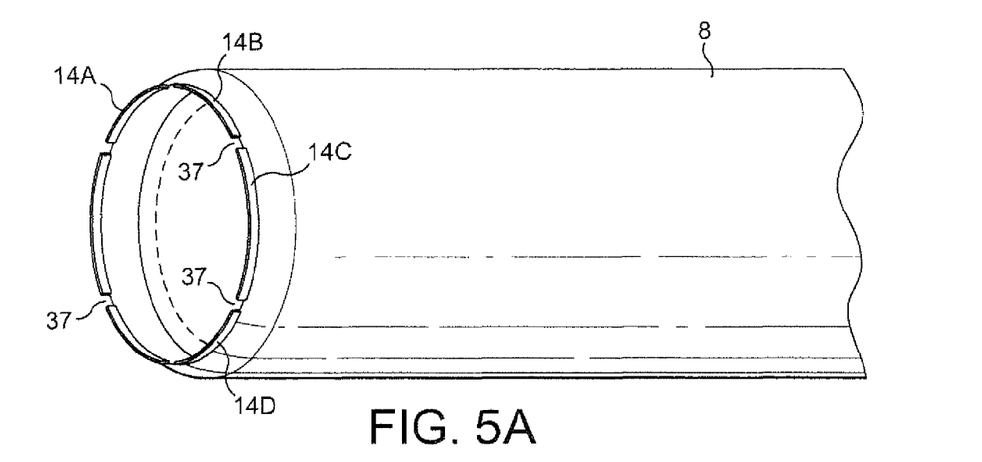
FIGS. 5A & 5B are enlarged views of different parts of a further embodiment of a morcellating device constructed in accordance with the invention.
Figure 5B:
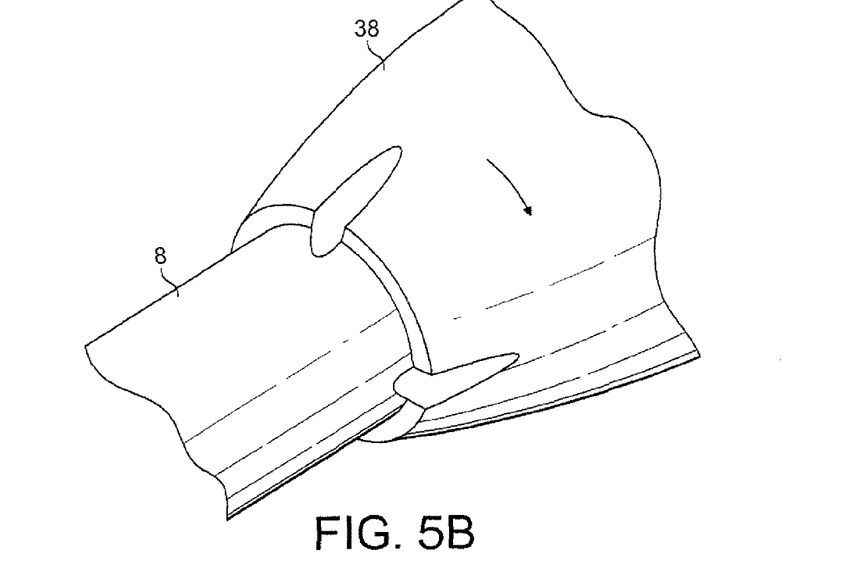

FIGS. 5A and 513 show an even more sophisticated arrangement, in which a series of active electrodes 14A, 14B, 14C, 14D etc. are disposed around the circumference of the tube 8, each active electrode being separated from circumferentially adjacent active electrodes by insulating spaces 37. Each active electrode 14A to 14D is provided with its own lead (not shown), so that any combination of active electrodes can be energised or not, depending on the circumstances. A rotatable collar 38 is provided on the tube 8, the collar having a series of contacts (not shown) on the inside thereof. Rotation of the collar 38 by the user of the device allows the user to select which active electrodes 14A to 14D are) energised. For example, rotation of the collar 38 to a first position sets the contacts such that every electrode 14A to 14D is energised, such that the anti-coring system is deactivated and the device cuts tissue around the entire circumference of the tube 8. Alternatively, rotating the collar 38 to a second position sets the contacts such that one electrode 14A is not energised, whereas each of the remaining electrodes 14B, 14C and 14D is energised. This inhibits cutting in the region of the electrode 14A, and provides the anti-coring action described previously. Rotating the collar 38 to a further position selects a different electrode 14B which is not energised, whereas each of the other electrodes 14A, 14C and 14D is energised. In this way, the orientation of the tube 8 can be varied, and yet an active electrode can be selected not to be energised, such that orientation of the anti-coring action remains constant with respect to the tissue being treated.

In an alternative arrangement, rotation of the collar 38 varies the number of active electrodes 14A to 14D that are not energised, rather than the position of the active electrode that is not energised. In this way, the user can vary the extent of the anti-coring action provided by the morcellating device 1.

Figure 6:
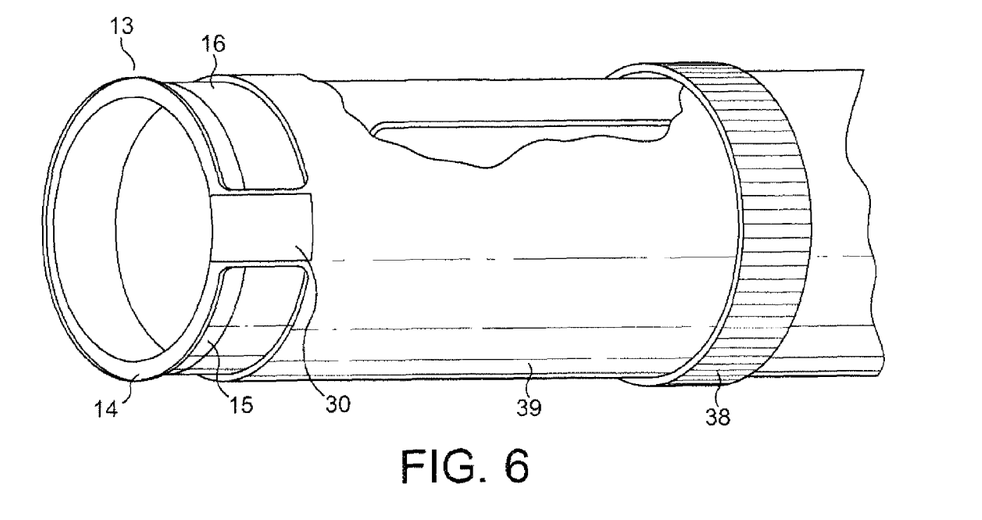
FIG. 6 is an enlarged view of yet another embodiment of a morcellating device constructed in accordance with the invention.

FIG. 6 shows an alternative embodiment in which a collar 38 is also provided, but in this embodiment the rotation of the collar causes a corresponding rotation of the electrosurgical assembly 13 at the distal end of the tube 8. The electrosurgical assembly 13 comprises a return electrode 16 which extends completely around the circumference of the tube 8, and an active electrode 14 which is interrupted in the region B by means of an insulated section 30. The electrosurgical assembly 13 is connected to the collar 38 by means of a sleeve 39, such that rotation of the collar causes a corresponding rotation of the electrosurgical assembly 13. The insulated section 30 can, therefore, be rotated between different angular positions, hence varying the angular position of the anti-coring effect described previously.

Figure 7:
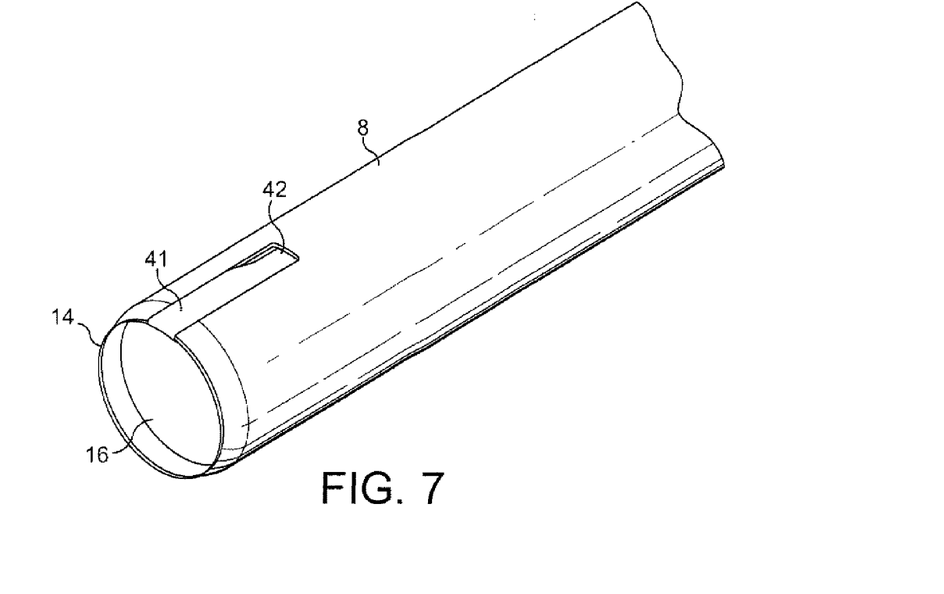
FIG. 7 is an enlarged perspective view of a further embodiment of a morcellating device constructed in accordance with the invention.
Figure 8:
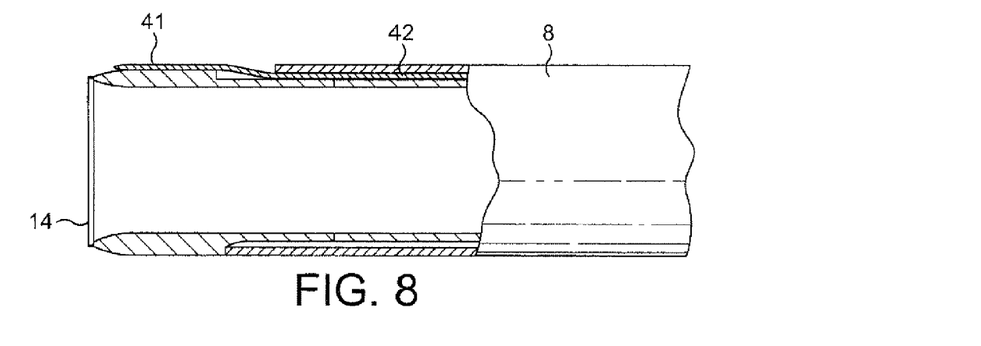
FIGS. 8 & 9 are enlarged views, partly in section, of the device of FIG. 7.
Figure 9:
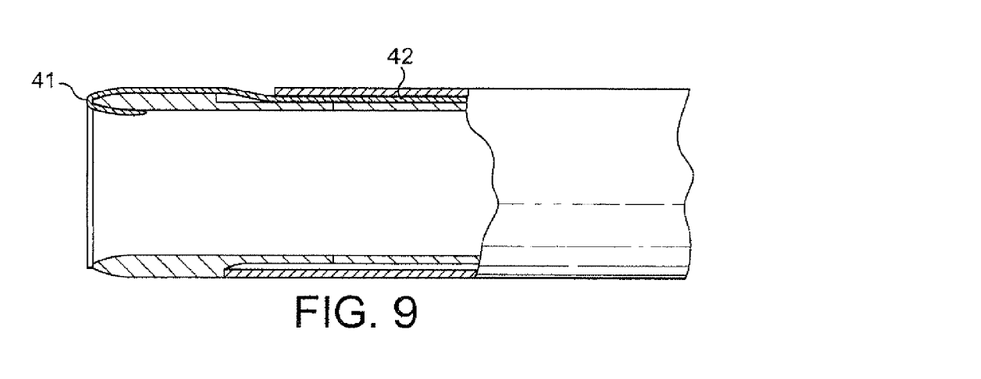

FIGS. 7 to 9 show a different arrangement in which both the active electrode 14 and the return electrode 16 extend completely around the circumference of the tube 8 at the distal end thereof. An electrically-insulating mask 41 is provided in a first circumferential region of the tube 8, so as to prevent the active electrode 14 from engaging tissue in that region. The mask 41 prevents tissue cutting in that region, and provides the anti-coring effect described previously. The mask 41 is typically an injection moulded polymer component, such as the polymer-nylon material "Zytel". In one arrangement, the mask 41 is disposed within a compartment 42 at the end of the tube 8, and can be selectively advanced and retracted by the operation of an actuating mechanism (not shown). When the mask 41 is advanced, it moves into a position obscuring the active electrode 14 in the first circumferential region, thereby providing the anti-coring effect described previously. When the mask 41 is retracted into the compartment 42, it allows the active electrode 14 to cut tissue around its entire circumference.

In an alternative arrangement, the mask 41 can be selectively attached or detached from the tube 8, depending on whether the anti-coring effect is desired by the user of the morcellating device 1, or whether maximum cutting effectiveness is required.

It will be appreciated by those skilled in the art that many minor modifications and alternative constructions can be envisaged, without departing from the scope of the present invention. For example, the tube 8 can be provided with a marker in alignment with the second circumferential region B, so as to highlight the position of that region to a user of the device. Providing an effective electrosurgical tissue-cutting assembly, in which a circumferential region of the cutting area is selectively inhibited, promotes the instrument to perform a peeling action on the tissue, and restricts the ability of the instrument to become buried in the tissue in a coring manoeuvre.

The invention claimed is:

1. A device for morcellating tissue within a body cavity of a patient, the morcellating device comprising a stationary tube having a distal end portion, the distal end portion including a stationary bipolar electrosurgical electrode assembly including a first active electrode located at the distal end of the tube, and a second return electrode axially set back from the active electrode and separated from the active electrode by an insulation member, the arrangement being such that, when an electrosurgical cutting voltage is applied to the electrode assembly, tissue can be pulled against the distal end of the tube to form a slug of resected tissue within the tube, wherein the bipolar electrosurgical assembly has a first circumferential region and a second circumferential region, the first circumferential region extending continuously around at least 50% of the circumference of the tube, the return electrode being present in both the first and second circumferential regions, the active electrode being present in the first circumferential region but disabled in the second circumferential region such that the bipolar electrosurgical assembly is adapted to cut tissue preferentially in the first circumferential region as compared with the second circumferential region.

2. A morcellating device according to claim 1, wherein the electrode is absent in the second circumferential region.

3. A morcellating device according to claim 2, wherein the second circumferential region comprises a third electrode spaced from both the first and second electrodes by one or more insulating sections.

4. A morcellating device according to claim 3, wherein the first, second and third electrodes each have separate leads connected thereto, such that the third electrode is capable of being selectively switched in and out of common electrical potential with that of at least one of either the first and second electrodes.

5. A morcellating device according to claim 1, wherein either the first electrode or the second electrode is split into three or more circumferential sections, each separated from adjacent circumferential sections by means of insulators.

6. A morcellating device according to claim 5, wherein the three or more circumferential sections each has a separate lead connected thereto, such that each circumferential section is capable of being switched into and out of common electrical potential with other circumferential sections.

7. A morcellating device according to claim 6, further comprising a switch capable of changing the circumferential section or sections that are switched out of common electric potential with the other circumferential sections.

8. A morcellating device according to claim 1, wherein the tube is provided with a marker in alignment with the second circumferential region, to highlight its position to a user of the device.

9. A morcellating device according to claim 1, wherein the active electrode is present in the second circumferential region but covered with an electrically-insulating mask.

10. A morcellating device according to claim 9, wherein the mask is selectively deployable between a first position in which it obscures the first electrode or the second electrode, and a second position in which it does not obscure the first electrode or the second electrode.

11. A morcellating device according to claim 10, wherein the mask is selectively advanced and retracted between the first and second positions.

12. A device for morcellating tissue within a body cavity of a patient, the morcellating device comprising:
a stationary tube having a distal end portion, the distal end portion including a stationary bipolar electrosurgical electrode assembly including first and second electrodes located at the distal end of the tube and separated one from the other by an insulation member, the arrangement being such that, when an electrosurgical cutting voltage is applied to the electrode assembly, tissue can be pulled against the distal end of the tube to form a slug of resected tissue within the tube, the bipolar electrosurgical assembly having a first circumferential region and a second circumferential region, the first circumferential region comprising first and second electrodes located at the distal end of the tube and being separated one from the other by at least one insulation member, the first circumferential region extending continuously around at least 50% of the circumference of the tube, the bipolar electrosurgical assembly being adapted to cut tissue preferentially in the first circumferential region as compared with the second circumferential region,
either the first electrode or the second electrode being split into three or more circumferential sections, each separated from adjacent circumferential sections by means of insulators, the three or more circumferential sections each having a separate lead connected thereto, such that each circumferential section is capable of being switched into and out of common electrical potential with other circumferential sections, and a switch capable of changing the circumferential section or sections that are switched out of common electric potential with the other circumferential sections, the switch comprising a rotatable collar carried on the device.

13. A device for morcellating tissue within a body cavity of a patient, the morcellating device comprising:

a stationary tube having a distal end portion, the distal end portion including a stationary bipolar electrosurgical electrode assembly including first and second electrodes located at the distal end of the tube and separated one from the other by an insulation member, the arrangement being such that, when an electrosurgical cutting voltage is applied to the electrode assembly, tissue can be pulled against the distal end of the tube to form a slug of resected tissue within the tube, the bipolar electrosurgical assembly having a first circumferential region and a second circumferential region, the first circumferential region comprising first and second electrodes located at the distal end of the tube and being separated one from the other by at least one insulation member, the first circumferential region extending continuously around at least 50% of the circumference of the tube, the bipolar electrosurgical assembly being adapted to cut tissue preferentially in the first circumferential region as compared with the second circumferential region, either the first electrode or the second electrode being split into three or more circumferential sections, each separated from adjacent circumferential sections by means of insulators, the three or more circumferential sections each having a separate lead connected thereto, such that each circumferential section is capable of being switched into and out of common electrical potential with other circumferential sections, a switch capable of changing the circumferential section or sections that are switched out of common electric potential with the other circumferential sections, and means for determining the orientation of the tube, and for activating the switch so as to vary the circumferential section or sections that are switched out of common electric potential with the other circumferential sections depending on the orientation of the tube, the means for determining the orientation of the tube and for activating the switch comprising a rotatable collar which is carried on the tube and which has a series of contacts on the inside thereof whereby rotating the collar to different positions determines which of the sections is not energized so that the orientation of the tube can be varied, and whereby by maintaining the non-energized section in a predetermined orientation can be maintained, regardless of which way the tube is oriented by a user.

* * * * *